(12) United States Patent
Iizuka et al.

(10) Patent No.: US 10,890,528 B2
(45) Date of Patent: Jan. 12, 2021

(54) FLUORESCENT TESTING SYSTEM, MOLECULAR TESTING METHOD, AND FLUORESCENT TESTING METHOD

(71) Applicants: SHARP KABUSHIKI KAISHA, Sakai (JP); The University of Tokyo, Tokyo (JP)

(72) Inventors: Kunihiko Iizuka, Sakai (JP); Yoshihisa Fujimoto, Sakai (JP); Soo-Hyeon Kim, Tokyo (JP); Teruo Fujii, Tokyo (JP)

(73) Assignees: SHARP KABUSHIKI KAISHA, Sakai (JP); The University of Tokyo, Tokyo (JP)

( * ) Notice: Subject to any disclaimer, the term of this patent is extended or adjusted under 35 U.S.C. 154(b) by 26 days.

(21) Appl. No.: 16/345,439

(22) PCT Filed: Jul. 20, 2017

(86) PCT No.: PCT/JP2017/026180
§ 371 (c)(1),
(2) Date: Apr. 26, 2019

(87) PCT Pub. No.: WO2018/078967
PCT Pub. Date: May 3, 2018

(65) Prior Publication Data
US 2019/0250102 A1    Aug. 15, 2019

(30) Foreign Application Priority Data
Oct. 27, 2016  (JP) .................................. 2016-211121

(51) Int. Cl.
*G01N 21/64* (2006.01)
*G01J 1/44* (2006.01)
(Continued)

(52) U.S. Cl.
CPC ...... *G01N 21/6428* (2013.01); *B01L 3/50273* (2013.01); *B01L 3/502715* (2013.01);
(Continued)

(58) Field of Classification Search
CPC .................................................. G01N 21/6454
See application file for complete search history.

(56) References Cited

U.S. PATENT DOCUMENTS 5,405,519 A   4/1995  Schwartz
5,599,664 A   2/1997  Schwartz
(Continued)

FOREIGN PATENT DOCUMENTS

JP    H11-503022 A    3/1999
JP    2002-350346 A   12/2002
(Continued)

OTHER PUBLICATIONS

Soo Hyeon Kim, Large-scale femtoliter droplet arrray for digital counting of single biomolecules, Lab on a Chip, Dec. 7, 2012, Iss.23, pp. 4986-4991.
(Continued)

*Primary Examiner* — Shawn Decenzo
(74) *Attorney, Agent, or Firm* — ScienBiziP, P.C.

(57) ABSTRACT

Provided are a fluorescent testing system, a molecular testing method, and a fluorescent testing method that can avoid enlargement and complication. A fluorescent testing system (1) includes: an excitation light source (23) that radiates excitation light (L1) to protein to which a fluorescent probe is added; a silicon integrated circuit (10) including a photon detection unit (13) that detects light by a photodiode (12); a holding layer (30) including a microwell (31) that is provided above the photodiode (12) and holds the protein to which the fluorescent probe is added; and a control unit (24) that causes the excitation light source (23) to radiate the
(Continued)

excitation light (L1) to the protein which. is held and to which the fluorescent probe is added and causes the photon detection unit (13), after extinguishment of the excitation light (L1), to detect fluorescence emitted from the protein to which the fluorescent probe is added.

5 Claims, 8 Drawing Sheets

(51) Int. Cl.
*G01N 21/03* (2006.01)
*G01N 21/85* (2006.01)
*C12Q 1/686* (2018.01)
*B01L 3/00* (2006.01)
*G01N 37/00* (2006.01)
*G01N 33/543* (2006.01)
*B01L 7/00* (2006.01)

(52) U.S. Cl.
CPC .............. *C12Q 1/686* (2013.01); *G01J 1/44* (2013.01); *G01N 21/03* (2013.01); *G01N 21/645* (2013.01); *G01N 21/8507* (2013.01); *G01N 33/543* (2013.01); *G01N 37/00* (2013.01); *B01L 3/502784* (2013.01); *B01L 7/52* (2013.01); *B01L 2200/0642* (2013.01); *B01L 2200/0673* (2013.01); *B01L 2300/047* (2013.01); *B01L 2300/0663* (2013.01); *G01J 2001/446* (2013.01); *G01N 2021/6482* (2013.01); *G01N 2201/12* (2013.01)

(56) References Cited

U.S. PATENT DOCUMENTS

| | | | |
|---|---|---|---|
| 5,720,928 A | 2/1998 | Schwartz | |
| 6,147,198 A | 11/2000 | Schwartz | |
| 6,150,089 A | 11/2000 | Schwartz | |
| 7,348,573 B2* | 3/2008 | King | G01N 21/645 250/458.1 |
| 9,778,191 B2* | 10/2017 | Hsieh | G01N 21/6454 |
| 9,797,837 B2* | 10/2017 | Kim | G01N 21/6454 |
| 9,921,157 B2* | 3/2018 | Rothberg | G01N 21/6428 |
| 9,945,781 B2* | 4/2018 | Rulison | G01J 3/2803 |
| 10,254,225 B2* | 4/2019 | Zhong | B01L 3/502715 |
| 2002/0070350 A1* | 6/2002 | Rushbrooke | G01N 21/6452 250/461.1 |
| 2002/0197634 A1* | 12/2002 | Emoto | C12Q 1/6825 435/6.11 |
| 2002/0197636 A1* | 12/2002 | Emoto | G01N 21/6428 435/6.11 |
| 2004/0224317 A1 | 11/2004 | Kordunsky et al. | |
| 2006/0088944 A1 | 4/2006 | Schwartz et al. | |
| 2011/0111968 A1* | 5/2011 | Okura | B01L 7/00 506/7 |
| 2011/0306143 A1* | 12/2011 | Chiou | B82Y 15/00 436/94 |
| 2015/0204785 A1 | 7/2015 | Kim et al. | |
| 2017/0030832 A1* | 2/2017 | Lin | G01N 21/6452 |
| 2018/0180547 A1* | 6/2018 | Cao | G01N 21/6454 |
| 2019/0003971 A1* | 1/2019 | Cao | B01L 3/502715 |
| 2019/0011366 A1* | 1/2019 | Cao | G01N 21/6458 |
| 2019/0106662 A1* | 4/2019 | Trainoff | C12M 23/12 |
| 2019/0249220 A1* | 8/2019 | Fujii | C12M 47/04 |
| 2019/0250102 A1* | 8/2019 | Iizuka | C12Q 1/686 |
| 2019/0285579 A1* | 9/2019 | Iizuka | G01N 27/44721 |
| 2019/0293563 A1* | 9/2019 | Chung | G01N 21/6452 |

FOREIGN PATENT DOCUMENTS

| | | |
|---|---|---|
| JP | 2007-504477 A | 3/2007 |
| JP | 2014-066687 A | 4/2014 |
| JP | 2015-055568 A | 3/2015 |
| WO | 1996/31522 A1 | 10/1996 |
| WO | 2014/034781 A1 | 3/2014 |

OTHER PUBLICATIONS

Hiroyuki Noji, "digital counting of single biomolecules", physics News, 2011, Parity vol. 27, No. 01, Jan. 2012, p. 75-77.
Monya Baker, "Digital PCR hits its stride," Nature Methods vol. 9, Jun. 2012, p. 541-544.

* cited by examiner

FLUORESCENT TESTING SYSTEM, MOLECULAR TESTING METHOD, AND FLUORESCENT TESTING METHOD

TECHNICAL FIELD

The present invention relates to a fluorescent testing system, a molecular testing method, and a fluorescent testing method that observe a fluorescent phenomenon from a test object such as a minute biological or nonbiological sample to thereby detect a specific test object.

BACKGROUND ART

As a method of collectively testing many cells by fluorescent test, for example, a method of the related. art disclosed in NPL 1 has been known.

A biomolecular detection method disclosed in NPL 1 is a method of dividing analyte solution into a significantly great number of microfluids, binarizing fluorescent signals output from the microfluids, and determining only "whether an analyte biomolecule exists or does not exist" to estimate a molecule concentration of the biomolecule in the analyte solution. The method is remarkably excellent in detection sensitivity and quantitativity in comparison with an existing method by analog measurement.

To detect the fluorescent signals from the microfluids, however, the number of microfluids that output the fluorescent signals needs to be counted by using a fluorescent microscope. Thus, there is a problem that an apparatus is enlarged and complicated.

Meanwhile, to detect DNA (deoxy ribo nucleic acid) with high sensitivity, for example, a PCP (polymerase chain reaction) method of amplifying a specific gene by PCR is often used. The DNA amplified by the PCR is quantified by an agarose gel electrophoretic method, a fluorescent probe method, or the like.

To detect the DNA (deoxy ribo nucleic acid) by using the PCR method with high accuracy and high sensitivity, a digital PCR method, for example, as described in NPL 1 and NPL 2, in which sample solution is separated into many chambers, the PCR is performed in each of the chambers, and the number of molecules of the initial DNA in the sample is estimated from the number of chambers in which the PCR is confirmed is also used.

With the digital PCR method, by confirming reaction after the PCR in the many chambers, an average number of samples is estimated from a proportion of positive chambers. It is known that, when a proportion of chambers exhibiting positive reaction in all the chambers is p and an average number of DNA existing in the chambers in an initial state is $\lambda$, the average number $\lambda$ is obtained by $$\lambda = -\ln(1-p)$$

based on a Poisson distribution. For example, as illustrated in FIG. 8(a), among 96 chambers, ones other than white circles are positive chambers and the number thereof is 96−35=61. As a result, $p=61/96=0.635$, and as illustrated in FIG. 8(b), $1-p=35/96=0.365$.

As a result, for example, when $\lambda$ is 7, a proportion of negative cells is less than 0.1%, and several thousand cells or more are necessary to significantly detect the number of negative cells. In a case where ten thousand cells are used, an upper limit of $\lambda$ that is able to be estimated is about 10. For $\lambda$ over the upper limit, probability of a negative cell is difficult to be significantly detected, so that estimation of $\lambda$ is not allowed.

On the other hand, in real-time PCR using the fluorescent probe method, an amplification process is proceeded while observing fluorescence and an initial number of samples is estimated from an arriving time to a detection threshold, so that a range of $\lambda$ that is able to be estimated is able to be enlarged remarkably. However, accuracy thereof is generally inferior to that of the digital PCR.

CITATION LIST

Non Patent Literature

NPL 1: Monya Baker, "Digital PCR hits its stride," Nature Methods VOL. 9, JUNE 2012, P. 541-544

NPL 2: Hiroyuki Noji, "digital counting of single biomolecules", physics News, 2011, Parity Vol 127, No. 01, 2012-01, P. 75-77

SUMMARY OF INVENTION

Technical Problem

In a fluorescent testing system of the related art disclosed in NPL 1 and 2 described above, however, a fluorescent microscope is used in digital measurement for collectively detecting fluorescent signals from many fine analytes, thus posing a problem that the fluorescent testing system is enlarged and complicated.

The invention is made in view of the aforementioned problems of the related art and an object thereof is to provide a fluorescent testing system, a molecular testing method, and a fluorescent testing method that can avoid enlargement and complication.

Solution to Problem

In order to solve the aforementioned problems, a fluorescent testing system in an aspect of the invention includes: an excitation light source that radiates excitation light to a test object; a silicon integrated circuit including a photon detection unit that detects light by a photodiode; a holding layer including a through hole that is provided above the photodiode and holds the test object; and a control unit that causes the excitation light source to radiate the excitation light to the test object that is held and causes the photon detection unit, after extinguishment of the excitation light, to detect fluorescence emitted from the test object.

In order to solve the aforementioned problems, a molecular testing method in an aspect of the invention includes performing polymerase chain reaction in a plurality of isolation rooms in parallel by using the fluorescent testing system described above.

In order to solve the aforementioned problems, a fluorescent testing method in an aspect of the invention is a fluorescent testing method using the fluorescent testing system described above, and includes: a photon detection step of detecting a photon of excitation light incident on the photodiode during irradiation of the excitation light; and a fluorescence detection step of detecting, after extinguishment of the excitation light, fluorescence emitted from the test object after the excitation light is radiated.

Advantageous Effects of Invention

According to an aspect of the invention, an effect of providing a fluorescent testing system, a molecular testing method, and a fluorescent testing method that can avoid enlargement and complication is exerted.

DESCRIPTION OF EMBODIMENTS

Embodiment 1

An embodiment of the invention will be described as follows with reference to FIGS. 1 and 2.

Configuration of Fluorescent Testing System

A configuration of a fluorescent testing system of the present embodiment will be described with reference to FIG. 2. FIG. 2 is a sectional view illustrating a configuration of an example of the fluorescent testing system of the present embodiment.

Figure 2:
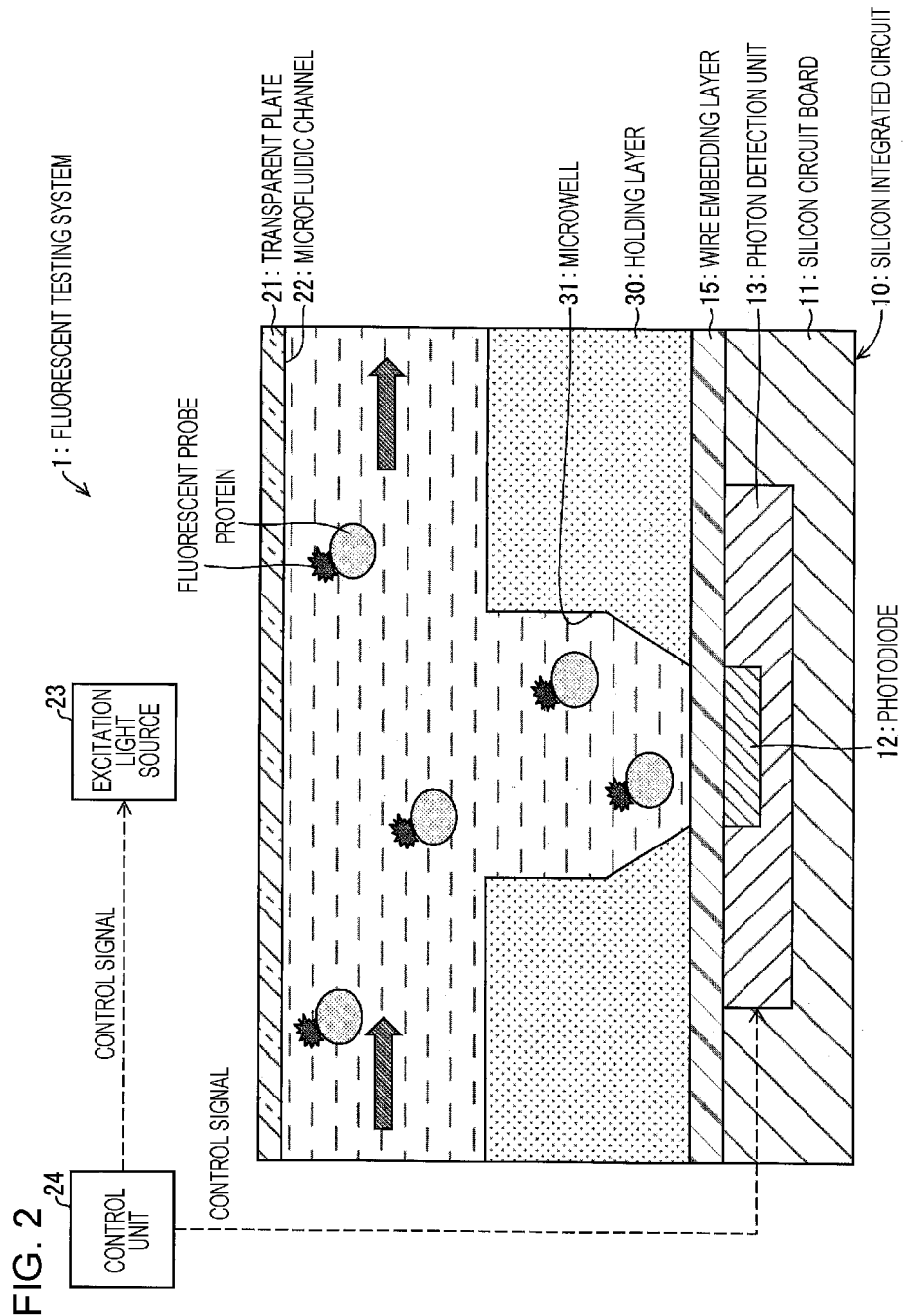
FIG. 2 is a sectional view illustrating a configuration of an example of the fluorescent testing system.

As illustrated in FIG. 2, a fluorescent testing system 1 of the present embodiment includes a silicon integrated circuit 10 provided with a photon detection unit 13 that detects light by a photodiode 12, a holding layer 30 by which, for example, protein as a test object is held above the photodiode 12, an excitation light source 23, and a control unit 24 that synchronously controls a light emission operation of the excitation light source 23 and a detection operation of the photon detection unit 13.

The silicon integrated circuit 10 is formed with a wire embedding layer 15 laminated on an upper side of a silicon circuit board 11.

In the silicon circuit board 11, a circuit constituted by the photodiode 12 and the photon detection unit 13 that detects light by using the photodiode 12 is formed. As the photodiode 12, for example, a single photon avalanche diode (SPAD) is usable.

A wire that is not illustrated is embedded in the wire embedding layer 15.

The holding layer 30 is provided on an upper side of the wire embedding layer 15 in the silicon integrated circuit 10 and the holding layer 30 includes a microwell 31 as a through hole.

The holding layer 30 is formed by a material, for example, such as polyimide, silicon dioxide ($SiO_2$), or dimethylpolysiloxane (PDMS). The holding layer 30 is preferably an opaque body.

The microwell 31 has, for example, a circular shape in a horizontal section and has, in a vertical section, an inverted truncated cone shape in which a bottom part is narrowed in the holding layer 30. Thereby, the microwell 31 has a capacity that enables to hold several proteins that are test objects.

Next, a transparent plate 21 as a lid is provided on an upper side of the holding layer 30, resulting that a microfluidic channel 22 that is a flow channel is formed between the holding layer 30 and the transparent plate 21. The microfluidic channel 22 is configured so that protein that is a test object flows therein.

In the present embodiment, the transparent plate 21 is configured to move to the holding layer 30 side.

The excitation light source 23 is provided above the transparent plate 21. The excitation light source 23 radiates excitation light through the transparent plate 21 toward the photodiode 12. As the excitation light source 23, for example, various light sources such as a semiconductor light emitting element (LED), an organic EL, and a semiconductor laser are usable. A plurality of light sources may be used.

In the present embodiment, the excitation light source 23 radiates the excitation light to, for example, protein that is the test object to emit fluorescence from the protein or a fluorescent probe added to the protein. Thus, for the excitation light source 23, for example, ultraviolet light, near-ultraviolet light, or visible light is used. That is, a phenomenon of the fluorescence is such that a molecule and an ion of the protein or the fluorescent probe added to the protein that absorb ultraviolet light, near-ultraviolet light, or visible light are excited, and then, the molecule and the ion are shifted to an intermediate excited state to emit light having a wavelength longer than that of the excitation light therefrom and are returned to a ground state. Thus, the wavelength of the excitation light which the excitation light source 23 radiates to the protein or the fluorescent probe added to the protein is required to include a component of a wavelength shorter than a wavelength of the fluorescence emitted from the protein or the fluorescent probe added to the protein.

The control unit 24 controls blinking of the excitation light source 23 and driving of the photon detection unit 13.

Meanwhile, in such a kind of fluorescent testing system of the related art, by utilizing a difference of the wavelength of the excitation light and the wavelength of the fluorescence, the excitation light and the fluorescence are separated by an optical filter to detect only the fluorescence. Thus, only a fluorescent material suitable for the incorporated filter is able to be used for the test and there is a problem that an application range of a type of the fluorescence is limited.

Here, an average time during which the excited state is returned to the ground state is called a fluorescent lifetime. In other words, the fluorescent lifetime is a time required for fluorescent intensity to be reduced to 1/e. Note that, the fluorescence does not disappear even when the time elapses. It is always possible to detect the fluorescence after extinguishment of the excitation light theoretically, if not practically. From a practical viewpoint, when the detection is performed as soon as possible after the extinguishment of the excitation light, the fluorescence is detected more easily because the fluorescent is strong. As a reference, it is desirable to perform the detection within a time period of a few times the fluorescent lifetime.

As a result, by using the fluorescent lifetime, fluorescence that is emitted is able to be observed after the extinguishment of the excitation light without using an optical filter that separates the excitation light and the fluorescence on the basis of the wavelengths.

Thus, the control unit 24 of the present embodiment controls the excitation light source 23 to radiate the excitation light to the protein as the test object that is held in the microwell 31 of the holding layer 30. Then, the control unit 24 stops lighting of the excitation light source 23. Next, the control unit 24 drives the photon detection unit 13 to measure the fluorescence emitted from the protein as the test object or the fluorescent probe added to the protein Specifically, the control unit 24 performs control so that the excitation light source 23 radiates the excitation light in a pulsed manner. Setting is performed in advance so that the photon detection unit 13 is driven in a light-off period of the pulse of the excitation light. As a result, only the fluorescence is emitted from the protein as the test object or the fluorescent probe added to the protein in a time period during which the photon detection unit 13 is driven, so that the photon detection unit 13 detects the fluorescence after the extinguishment of the excitation light without using an optical filter.

Measurement Operation Of Fluorescent Testing System

A specific operation when a test object is measured by using the fluorescent testing system 1 having the configuration described above will be described with reference to FIGS. 1 and 2. FIG. 1 is a sectional view illustrating a state where solution that includes protein as a test object and a fluorescent probe added to the protein flows in the microfluidic channel 22 on the silicon integrated circuit 10 and the protein and the fluorescent probe are held in the microwell 31 in the fluorescent testing system 1 in the present embodiment. Note that, description will be given by assuming that the test object is, for example, specific protein to which a fluorescent probe is added in the present embodiment.

As illustrated in FIG. 2, the protein which is the test object and to which the fluorescent probe is added is supplied to the microfluidic channel 22 between the wire embedding layer 15 and the transparent plate 21 provided above the wire embedding layer 15. Thereby, the protein to which the fluorescent probe is added is held in the microwell 31 of the holding layer 30.

Figure 1:
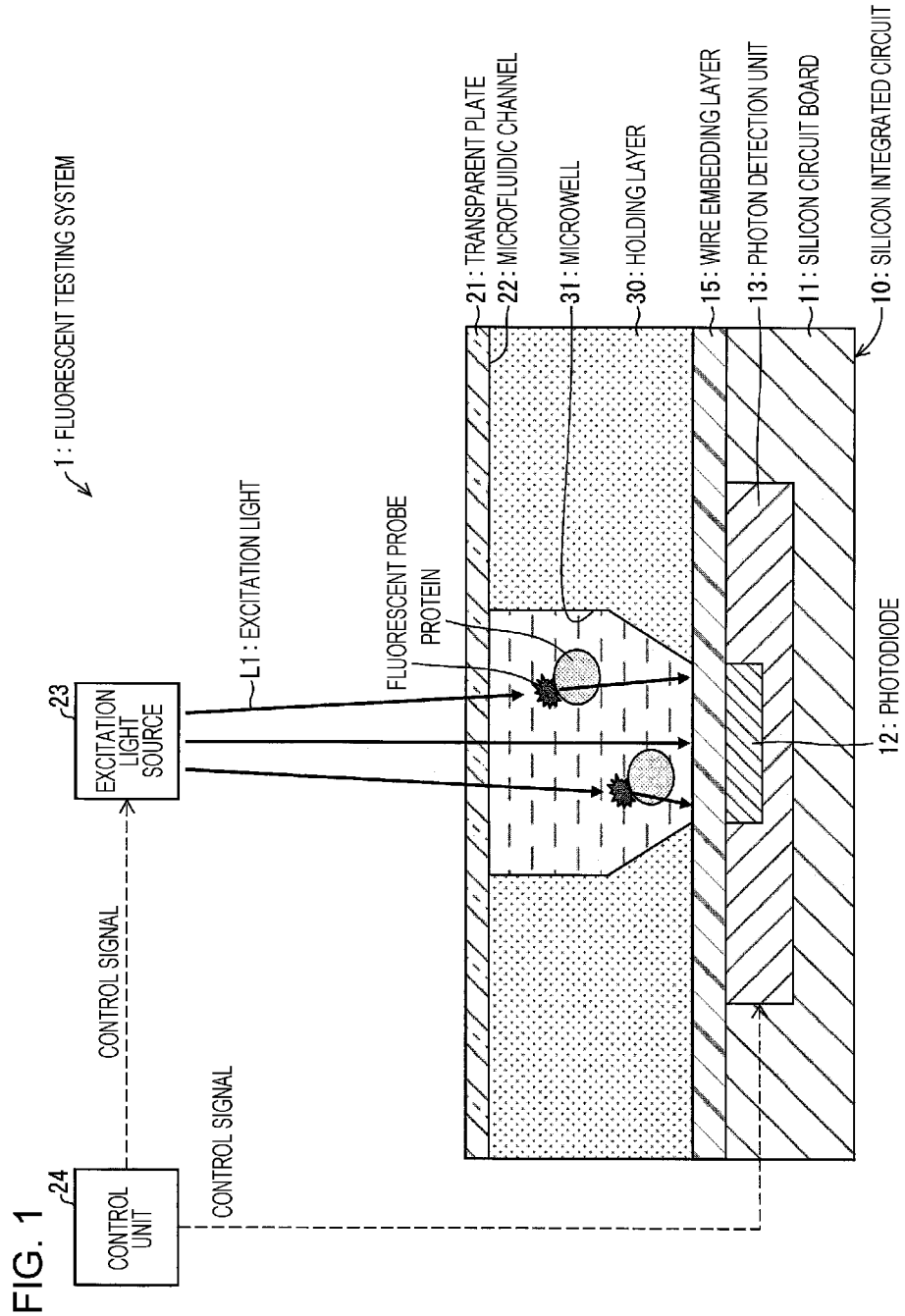
FIG. 1 illustrates a configuration of a fluorescent testing system in Embodiment 1 of the invention and is a sectional view illustrating a state where solution including a test object flows in a microfluidic channel on a silicon integrated circuit and the test object is held in a microwell.

In such a state, as illustrated in FIG. 1, the transparent plate 21 is pressed down to form a chamber in which a lid is put on the microwell 31. This provides a state where a plurality of proteins to which the fluorescent probe is added are filled in the microwell 31 of the holding layer 30.

Next, the control unit 24 causes the excitation sight source 23 to be turned on, and turned off after a fixed time period, and then, drives the photon detection unit 13 to detect fluorescence that continues to emit light while being attenuated. Specifically, the excitation light source 23 radiates excitation light L1 toward the microwell 31 by switching on and off the excitation light L1 in the pulsed manner. Then, in an on period of the excitation light source 23, the fluorescent probe added to the specific protein that is a measurement object absorbs the excitation light L1 from the excitation light source 23. Thereby, the fluorescent probe emits the fluorescence. At this time, the excitation light L1 is also radiated. Thus, in the present embodiment, since the excitation light source 23 radiates the excitation light L1 in the pulsed manner, the excitation light L1 is sometimes extinguished. Thereby, the photon detection unit 13 is driven during a time period when the excitation light L1 is extinguished and the fluorescence is continuously provided, and only the fluorescence is received by the photon detection unit 13, so that only the fluorescence is able to be detected.

In this manner, the fluorescent testing system 1 of the present embodiment includes the excitation light source 23 that radiates the excitation light L1 to the protein which is the test object and to which the fluorescent probe is added, the silicon integrated circuit 10 including the photon detection unit 13 that detects light by the photodiode 12, the holding layer 30 including the microwell 31 as the through hole that is provided above the photodiode 12 and holds the protein to which the fluorescent probe is added, and the control unit 24 that causes the excitation light source 23 to radiate the excitation light L1 to the protein which is held and to which the fluorescent probe is added and causes the photon detection unit 13 to detect, after the extinguishment of the excitation light L1, the fluorescence emitted from the protein to which the fluorescent probe is added.

As a result, after the extinguishment of the excitation light L1, only the fluorescence is detected by the photon detection unit 13. Thus, only the fluorescence emitted from the protein to which the fluorescent probe is added is able to be measured without separating the excitation light L1 and the fluorescence by an optical filter. Accordingly, since it is not necessary to use an optical filter corresponding to a type of the fluorescence, the fluorescent testing system 1 is able to be prevented from being complicated.

In the fluorescent testing system 1 of the present embodiment, the photon detection unit 13 by the photodiode 12 is integrated in the silicon integrated circuit 10, and the chamber formed by the microwell 31 that is minute is formed above the photodiode 12, so that a fluorescent signal from the protein which is held in the chamber and to which the fluorescent probe is added is able to be automatically detected.

As a result, neither a fluorescent microscope that causes enlargement and complication of the fluorescent testing system 1 nor image processing for counting the number of times of detection from a fluorescent image that is observed is required, so that digital measurement such as counting of a desired test object is able to be easily performed.

Accordingly, it is possible to provide the fluorescent testing system 1 that can avoid enlargement and complication.

Embodiment 2

Another embodiment of the invention will be described as follows with reference to FIGS. 3 and 4. Note that, the present embodiment is the same as Embodiment 1 described above other than a configuration described in the present embodiment. For convenience of description, members having the same functions as those of the members illustrated in the figures of Embodiment 1 described above will be given the same reference signs and description thereof will be omitted.

A fluorescent testing system 2 of the present embodiment is different in that, in addition to the configuration of the fluorescent testing system 1 of Embodiment 1 described above, a plurality of first and second photon detection units 13a and 13b are provided, a transparent plate 42 is formed by a lid 42a and a partition wall 42b, and a part of a holding layer 40 is made from silicon dioxide ($SiO_2$).

Configuration of Fluorescent Testing System

A configuration of the fluorescent testing system 2 of the present embodiment will be described with reference to FIG. 3. FIG. 3 is a sectional view illustrating the configuration of the fluorescent testing system 2 in the present embodiment. Note that, the excitation light source 23 and the control unit 24 are omitted in FIG. 3.

Figure 3:
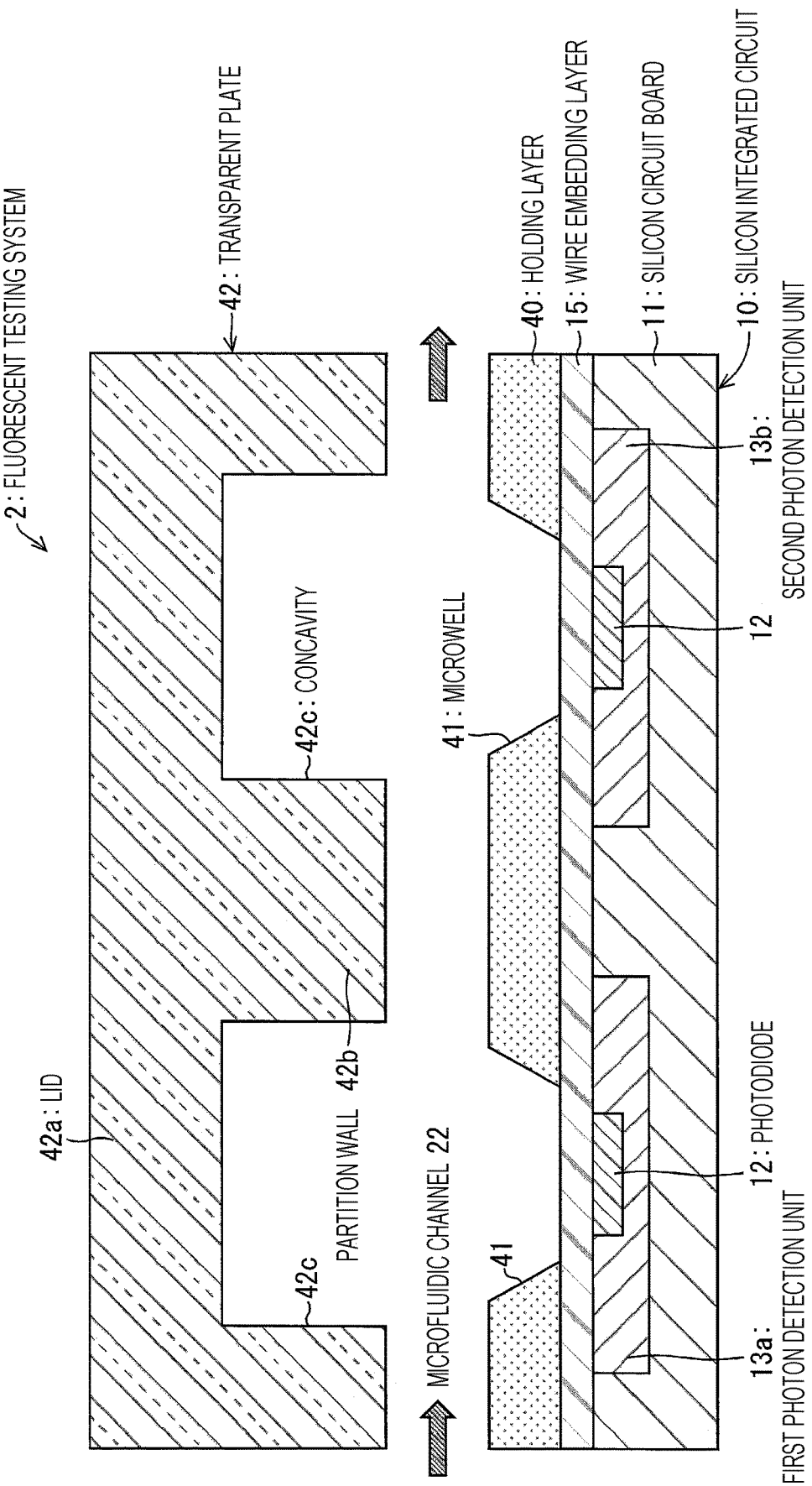
FIG. 3 illustrates a configuration of a fluorescent testing system in Embodiment 2 of the invention and is a sectional view illustrating the configuration of the fluorescent testing system.
Figure 4:
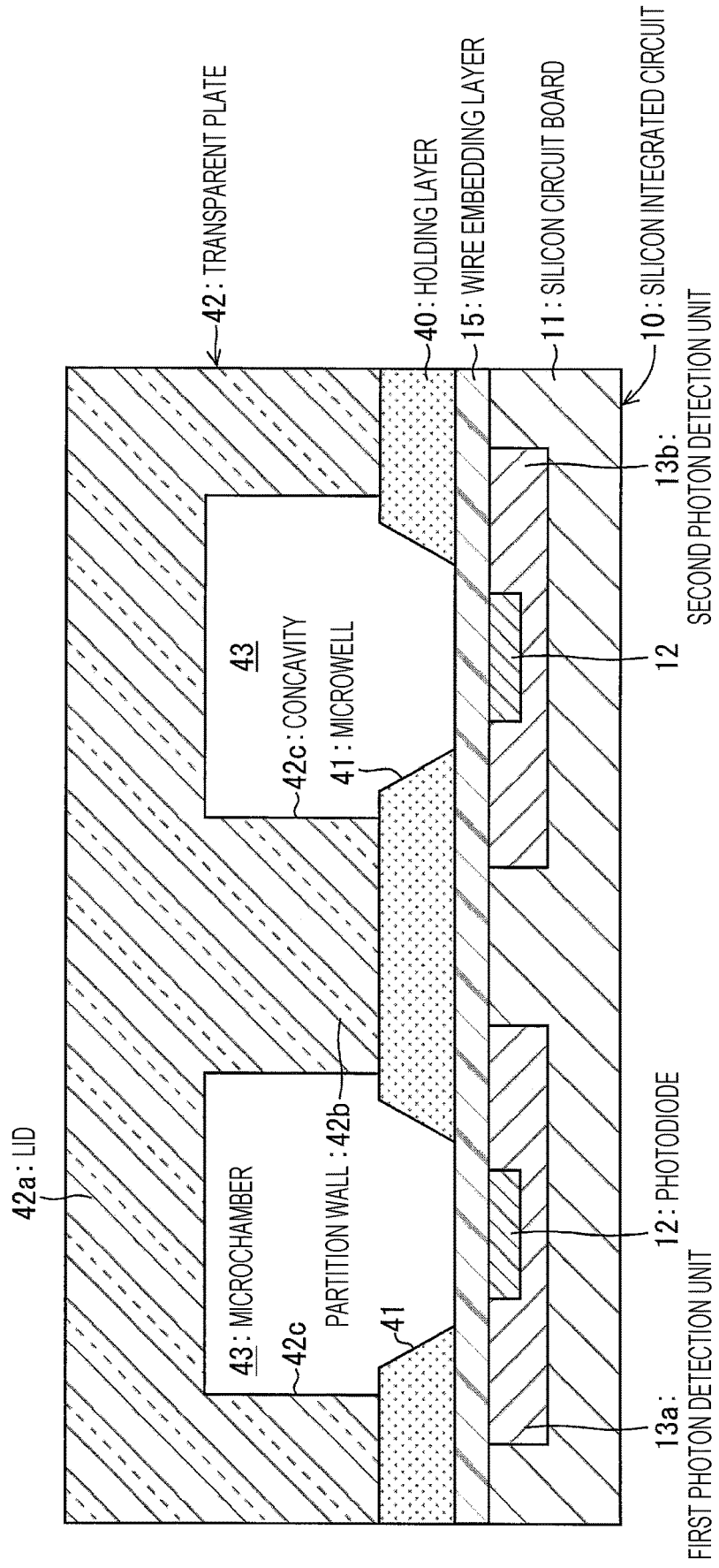
FIG. 4 illustrates a state where a test object is measured by using the fluorescent testing system and is a sectional view illustrating a state where a transparent plate is moved to a holding layer side and a microchamber that isolates the test object is formed.

As illustrated in FIG. 3, the fluorescent testing system 2 of the present embodiment includes, in addition to the configuration of the fluorescent testing system 1 of Embodiment 1 described above, the plurality of first and second photon detection units 13a and 13b. Thereby, microwells 41 and 41 are respectively formed above the first photon detection unit 13a and the second photon detection unit 13b in the holding layer 40. This makes it possible to have test objects tested at the same time at a plurality of places, the first photon detection unit 13a and the second photon detection unit 13b. Note that, the number of photon detection units is two of the first photon detection unit 13a and the second photon detection unit 13b in the present embodiment, but is not limited thereto and may be two or more.

A part of the holding layer 40 is made from silicon dioxide ($SiO_2$) in the present embodiment. Specifically, a part of the holding layer 40, which is near the photodiode 12, is made from silicon dioxide ($SiO_2$). Thereby, the holding layer 40 is able to prevent stray light such as external light other than the fluorescence from being incident on the photodiode 12 by blocking the stray light and prevent the fluorescence other than one emitted from the test object from being incident on the photodiode 12 because the silicon dioxide ($SiO_2$) has less autofluorescence.

In the present embodiment, the transparent plate 42 as the lid provided above the holding layer 40 is formed by the lid 42a and the partition wall 42b. As a result, the lid 42a and the partition wall 42b form a concavity 42c as a recess. In the present embodiment, the transparent plate 42 is movable toward the holding layer 40. As a result, as illustrated in FIG. 4 described below, by moving transparent plate 42 to make the partition wall 42b contact with the holding layer 40, a microchamber 43 as an isolation room that isolates the test object is formed by the concavity 42c and a microwell 41 of the holding layer 40.

Measurement peration of fluorescent Testing System

A measurement Operation in the Fluorescent Testing system 2 having the configuration described above will be described with reference to FIGS. 3 and 4. FIG. 4 illustrates a state where a test object is measured by using the fluorescent testing system 2 and is a sectional view illustrating a state where the transparent plate 42 is moved to the holding layer 40 side and the microchamber 43 that isolates the test object is formed. Note that, the excitation light source 23 and the control unit 24 are omitted in FIG. 4.

In the fluorescent testing system 2 having the configuration described above, as illustrated in FIG. 3, not-illustrated protein which is a test object and to which a fluorescent probe is added is supplied to the microfluidic channel 22 between the wire embedding layer 15 and the transparent plate 42 provided above the wire embedding layer 15. In such a state, as illustrated in FIG. 4, the transparent plate 42 is pressed down and a bottom surface of the partition wall 42b is brought into close contact with the holding layer 40 in which the microwell 41 is formed and which is made from silicon dioxide (Sift). Thereby, the microchamber 43 is formed by the concavity 42c and the microwell 41. As a result, the not-illustrated protein to which the fluorescent probe is added is filled in the microchamber 43.

Here, since the holding layer 40 made from silicon dioxide ($SiO_2$) does not emit fluorescence, there is no possibility of confusion with fluorescence from the fluorescent probe added to the protein and improvement of accuracy of detection of the fluorescence is expected. Though it is difficult to form a deep microwell 41 in the holding layer 40 made from silicon dioxide ($SiO_2$), it is possible to increase a depth of the microchamber 43 with the concavity 42c formed on a side of the transparent plate 42.

In this manner, in the fluorescent testing system 2 in the present embodiment, at least a part of the holding layer 40 is formed by using silicon dioxide ($SiO_2$).

For example, in a case where the holding layer 40 is formed by a material that emits fluorescence, both the fluorescence from the test object and the fluorescence from the holding layer 40 are incident on the photodiode 12, so that the fluorescence from the test object is not able to be accurately detected.

On the other hand, since silicon dioxide ($SiO_2$) does not emit fluorescence, there is no possibility of confusion with the fluorescence from the fluorescence included in the test object and it is possible to achieve improvement of accuracy of detection of the fluorescence.

In the fluorescent testing system 2 in the present embodiment, the transparent plate 42 that has the partition wall 42b and serves as the lid is provided so as to be moveable toward a direction of the holding layer 40, and when the transparent plate 42 is moved to make the bottom surface of the partition wall 42b contact with the holding layer 40, the microchamber 43 as the isolation room that isolates the test object is formed by the concavity 42c, which is formed by the transparent plate 42 having the partition wall 42b, and the microwell 41 of the holding layer 40.

Thereby, though it is difficult to form a deep microwell 41 in the holding layer 40 made from silicon dioxide ($SiO_2$), it is possible to increase the depth of the microchamber 43 as the chamber that is the isolation room with the concavity 42c formed by the transparent plate 42 that faces the holding layer 40 and has the partition wall 42b.

Embodiment 3

A still another embodiment of the invention will be described as follows with reference to FIG. 5. Note that, the present embodiment is the same as Embodiments 1 and 2 described above other than a configuration described in the present embodiment. For convenience of description, members having the same functions as those of the members illustrated in the figures of Embodiments 1 and 2 described above will be given the same reference signs and description thereof will be omitted.

A fluorescent testing system 3 of the present embodiment is different in that, in addition to the configurations of Embodiments 1 and 2 described above, a heater 52 and a temperature sensor 53 are provided in the silicon integrated circuit 10.

Configuration of Fluorescent Testing System

A configuration of the fluorescent testing system 3 of the present embodiment will be described with reference to FIG. 5. FIG. 5 is a sectional view illustrating the configuration of the fluorescent testing system 3 of the present embodiment. Note that, the excitation light source 23 and the control unit 24 are omitted in FIG. 5.

Figure 5:
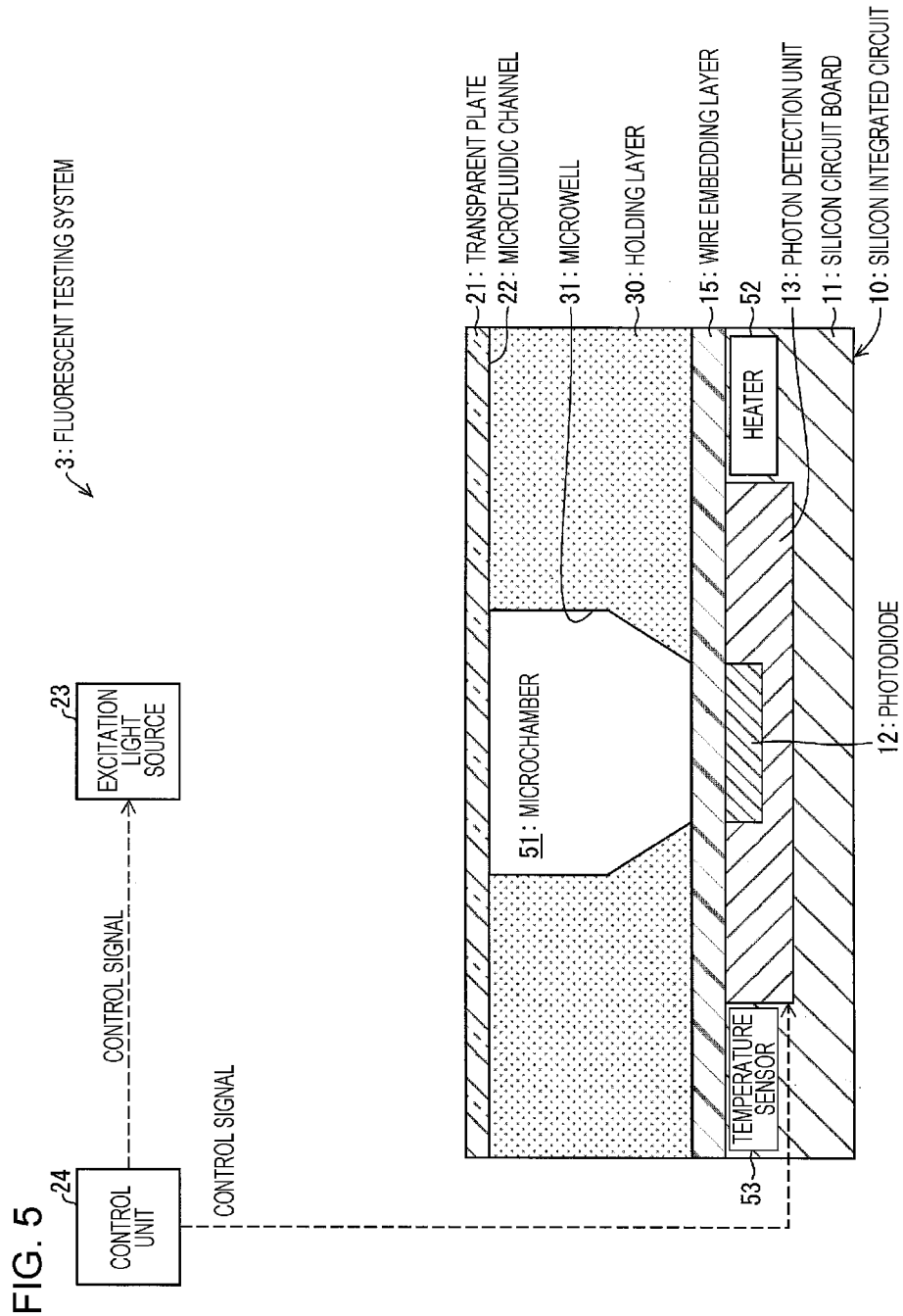
FIG. 5 illustrates a fluorescent testing system of Embodiment 3 of the invention and is a sectional view illustrating a configuration of the fluorescent testing system.

In the fluorescent testing system 3 of the present embodiment, as illustrated in FIG. 5, the heater 52 and the temperature sensor 53 are built in the silicon integrated circuit 10.

That is, as a PCR (polymerase chain reaction) cycle for amplifying DNA. (deoxy ribo nucleic acid) by using a PCR method in a microchamber 51, three cycles in which a temperature of solution in the microchamber 51 is set to about 94° C., about 60° C., and about 72° C. are required.

Thus, in the fluorescent testing system 3 of the present embodiment, the heater 52 and the temperature sensor 53 are built in the silicon integrated circuit 10, so that temperature control of a limited region including sample solution included in the microchamber 51 is performed. As a result, accurate control is able to be performed at a higher speed in comparison with a case of the related art where a temperature of an environment including a device is controlled.

For example, the heater 52 periodically applies a voltage to a resistance element and changes a duty thereof to thereby control a heat generation amount.

Measurement Operation of Fluorescent Testing System

A measurement operation by the fluorescent testing system 3 of the present embodiment will be described with reference to FIG. 5.

First, solution in which a test object, polymerase, a primer, and a fluorescent probe are mixed is caused to flow in the microfluidic channel 22, the lid is put with use of the transparent plate 21, and the test object to which the fluorescent probe is added is held in the microchamber 51. In such a state, the DNA is amplified by the PCR method.

Specifically, the following steps are performed.

(1) (Thermal denaturation) Heating is performed by the heater 52 while the temperature is monitored by the temperature sensor 53, and the temperature of the solution in the microchamber 51 is controlled to be about 94° C. Thereby, double-stranded DNA is subjected to thermal denaturation and dissociated into single-stranded DNA.

(2) (Annealing) A heat generation amount of the heater 52 is reduced to reduce the temperature of the solution in the microchamber 51 to about 60° C. Thereby, the primer binds to the single-stranded DNA.

(3) (Extension reaction) The heat generation amount of the heater 52 is increased to change the temperature of the solution in the microchamber 51 to about 72° C. Thereby, a complementary strand is synthesized with the polymerase on the basis of a base sequence of the original DNA.

By repeating a series of processes of (1), (2), and (3) described above, the DNA is amplified double. The series of processes is called a single PCR amplification process.

Each time the single PCR amplification process is performed, fluorescent test is performed similarly to the case of Embodiment 1, and the number of times of the PCR amplification process required until a fluorescent amount of each microchamber 51 exceeds a predetermined threshold is measured.

On the other hand, the PCR amplification process is repeatedly performed for a serially diluted standard sample and intensity of fluorescence reaction in each process is measured.

Thereby, a relationship between the number of times of the PCR amplification process required until a fluorescence output exceeds a threshold and an initial number of DNA is able to be estimated.

When the microchamber 51 whose reaction is negative to the last exists in an amount of 1% or more, for example, the initial number of DNA $\lambda$ is estimated by $$\lambda = -\ln(n),$$

where n is a proportion of the negative microchamber 51.

When all the microchambers 51 are positive, the initial number of DNA is estimated as an average of the initial numbers of DNA estimated in the microchambers 51.

In the fluorescent testing system 3 of the present embodiment, measurement values of many microchambers 51 are averaged, so that the initial number of DNA is able to be estimated with high accuracy, in comparison with a normal real-time PCR method. Moreover, the initial number of DNA is able to be estimated even when there is no negative chamber and a range (dynamic range) of a concentration of DNA to which test is applicable is able to be enlarged, in comparison with a known digital PCR method.

In this manner, in a molecular testing method in the present embodiment, by using the fluorescent testing system 1 or 2, gene amplification reaction such as polymerase chain reaction is performed in a plurality of microchambers 51 in parallel.

As a result, since measurement values in many chambers are averaged, the initial number of DNA is able to be estimated with high accuracy, in comparison with gene amplification reaction in which a specific gene is amplified by using normal gene amplification reaction such as polymerase chain reaction.

Further, in comparison with the known digital POR method, the initial number of DNA is able to be estimated even when there is no negative chamber. As a result, a dynamic range of a concentration of DNA to which test is applicable is able to be enlarged.

Thus, it is possible to provide the molecular testing method using the fluorescent testing system that can avoid enlargement and complication.

Embodiment 4

A still another embodiment of the invention will be described as follows with reference to FIG. 6. Note that, the present embodiment is the same as Embodiment 1 described above other than a configuration described in the present embodiment. For convenience of description, members having the same functions as those of the members illustrated in the figures of Embodiment 1 described above will be given the same reference signs and description thereof will be omitted.

In the present embodiment, a molecular testing method in which, by using the fluorescent testing system 1 indicated in Embodiment 1 described above, detection and quantification of specific protein are performed with higher sensitivity and higher accuracy in comparison with a known ELISA method will be described.

The molecular testing method of the present embodiment will be described with reference to FIG. 6. FIG. 6 is a sectional view of the fluorescent testing system 1 for explaining the molecular testing method of the present embodiment.

Figure 6:
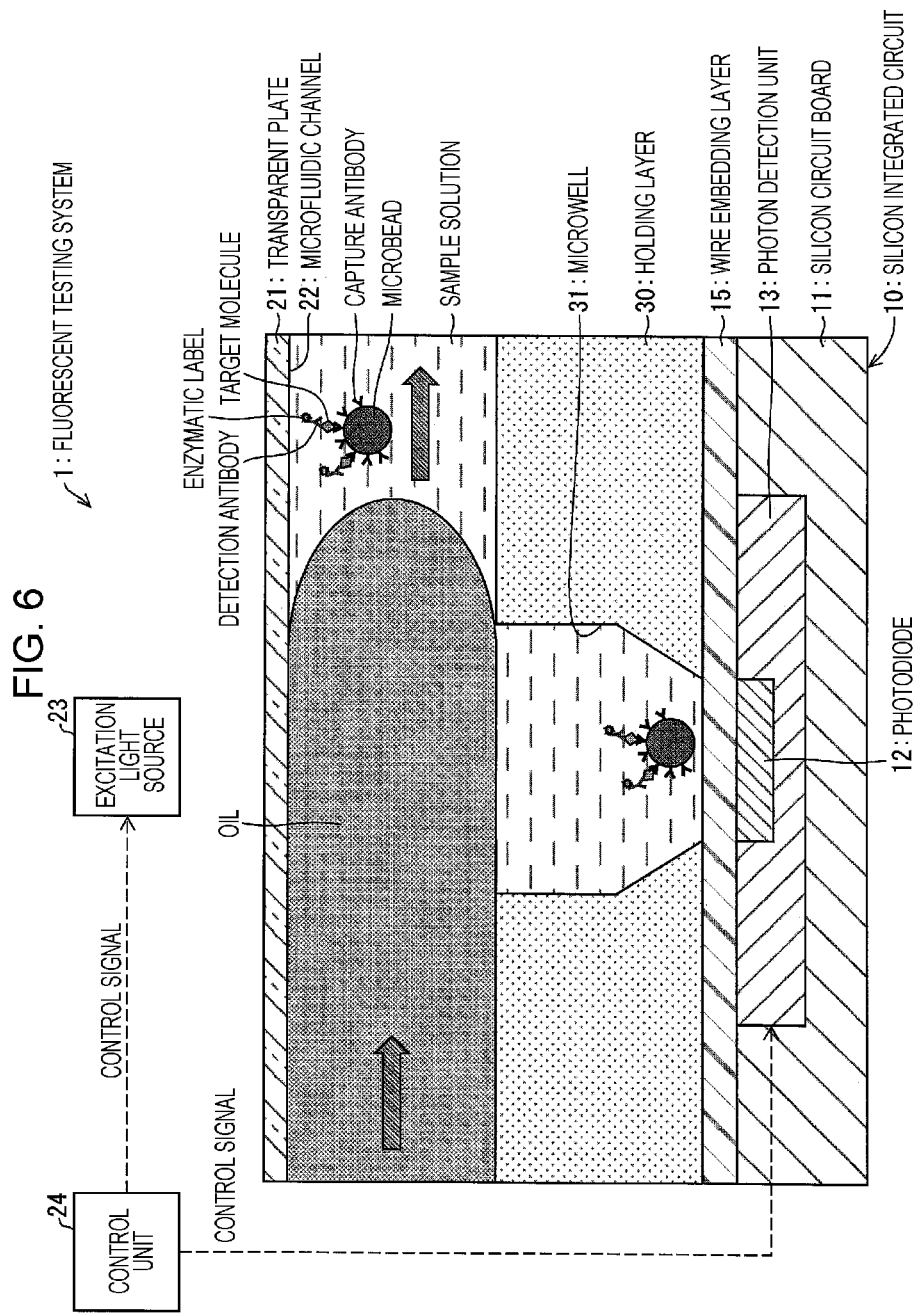
FIG. 6 illustrates a molecular testing method of Embodiment 4 of the invention and is a sectional view illustrating a configuration of the fluorescent testing system.

The molecular testing method of the present embodiment uses the fluorescent testing system indicated in Embodiment 1 as illustrated in FIG. 6.

Specifically, a microbead having a capture antibody is mixed with a detection antibody and a target molecule that is captured is further combined with the detection antibody. The detection antibody is labeled in advance by an enzymatic label, for example, such as alkaline phosphatase (AP), horseradish peroxidase (HRP), or P-galactosidase.

When solution thereof is caused to flow in the microfluidic channel 22 and a fluorescent substrate that is not illustrated is then caused to flow in the microfluidic channel 22, the fluorescent substrate reacts with the enzymatic label to generate a fluorescent material that is not illustrated. Next, when oil is caused to flow in the microfluidic channel, a lid of an oil layer is put on the microwell 31, so that each microwell 31 forms an independent microchamber. As a result, the fluorescence is detected from the photodiode 12 below the microchamber in which the microbead capturing the target molecule is captured, and the number of target molecules is estimated from a quantity of light in the photodiode from which the fluorescence is detected.

Since the generation of the fluorescent material is performed in a limited region of the microchamber, the fluorescence is generated intensively on the photodiode 12 and the detection is able to be performed even when the number of target molecules is small.

Such a molecular testing method of the related art has been performed by using a fluorescent microscope, however, according to the present embodiment, neither fluorescent microscope nor image processing of a captured image thereof is necessary. Therefore, it is possible to observe in real time a state where the fluorescence increases in a process where the fluorescent material is generated when the fluorescent substrate reacts with the enzymatic label and measure not only the number of photodiodes 12 from which the fluorescence is detected but also a time when a quantity of the fluorescence exceeds a predetermined threshold. Thereby, an amount of the target molecule captured in each of the microchambers is able to be estimated and the concentration of the target molecule is able to be estimated more accurately.

In this manner, the molecular testing method in the present embodiment includes a first step of mixing a microbead having a capture antibody with a detection antibody, further combining a captured target molecule with the detection antibody, and causing solution, which includes the microbead, to flow in the microfluidic channel 22 provided in the fluorescent testing system 1, a second step of causing a fluorescent substrate to flow in the microfluidic channel 22, a third step of causing oil to flow in the microfluidic channel, and a fourth step of detecting, by the fluorescent testing system 1, a fluorescent material generated when the fluorescent substrate reacts with an enzymatic label.

As a result, it is possible to provide the molecular testing method in which detection and quantification of specific protein are performed with higher sensitivity and higher accuracy in comparison with a known ELISA method. Further, it is possible to provide the molecular testing method using the fluorescent testing system that can avoid enlargement and complication.

Embodiment 5

Figure 7:
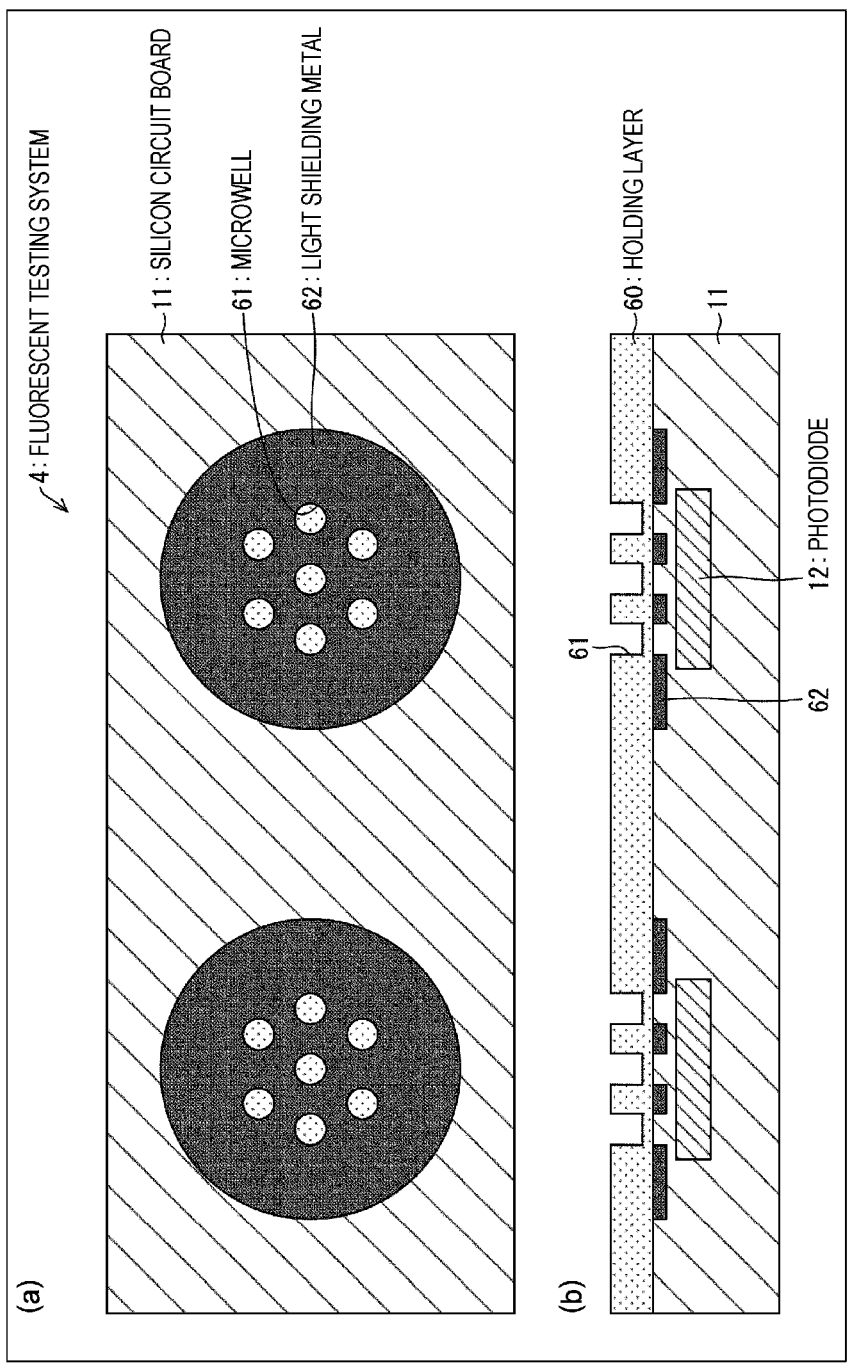
FIG. 7(a) illustrates a fluorescent testing system of Embodiment 5 of the invention and is a plan view illustrating a configuration of the fluorescent testing system in which a holding layer is omitted and FIG. 7(b) illustrates the configuration of the fluorescent testing system and is a sectional view illustrating a silicon circuit board in which a light shielding metal is arranged in a region other than a part directly below microwells.
Figure 8:
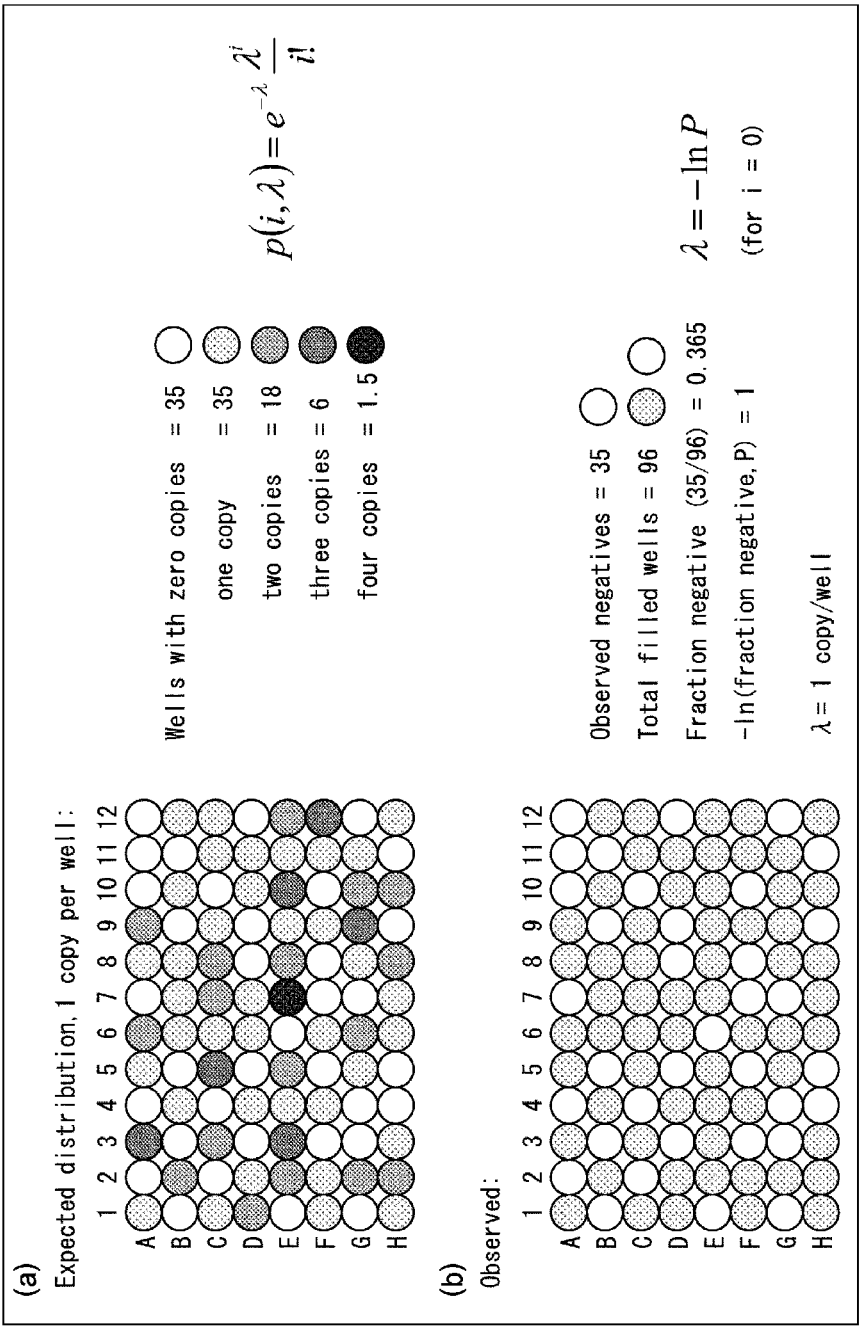
FIGS. 8(a) and 8(b) illustrate a method of estimating the number of molecules of initial DNA in a sample by a known digital PCR method.

A still another embodiment of the invention will be described as follows with reference to FIG. 7. Note that, the present embodiment is the same as Embodiment 4 described above other than a configuration described in the present embodiment. For convenience of description, members having the same functions as those of the members illustrated in the figure of Embodiment 4 described above will be given the same reference signs and description thereof will be omitted.

A fluorescent testing system 4 and a fluorescent testing method in the present embodiment include a configuration and a step of detecting fluorescence after extinguishment of excitation light, similarly to the fluorescent testing systems 1 to 3 of Embodiments 1 to 4 described above. Additionally, a difference lies in that the fluorescent testing system 4 and the fluorescent testing method in the present embodiment further include a configuration and a step of detecting a photon of excitation light incident on the photodiode 12 during irradiation of the excitation light.

The fluorescent testing system 4 of the present embodiment will be described with reference to FIGS. 7(a) and 7(b). FIG. 7(a) illustrates the fluorescent testing system 4 of the present embodiment and is a plan view illustrating a configuration of the fluorescent testing system 4 in which a holding layer 60 is omitted. FIG. 7(b) illustrates the configuration of the fluorescent testing system 4 and is a sectional view illustrating the silicon circuit board 11 in which a light shielding metal 62 is arranged in a region other than a part directly below microwells 61.

In the fluorescent testing system 4 of the present embodiment, as illustrated in FIGS. 7(a) and 7(b), a plurality of microwells 61 are formed above each of photodiodes 12. A size of each of the microwells 61 is a size by which one microbead described in Embodiment 4 can be captured but a plurality of microbeads are difficult to be captured.

In the fluorescent testing system 4 of the present embodiment, the light shielding metal 62 as a metal layer for light shielding is formed above the photodiode 12 other than the part directly below the microwells 61 as through holes.

The fluorescent testing system 4 and the fluorescent testing method using the same in the present embodiment further include, in addition to the configuration and the step of detecting fluorescence after extinguishment of excitation light, a photon detection step of detecting a photon of the excitation light incident on the photodiode 12 during irradiation of the excitation light.

That is, in the present embodiment, the plurality of microwells 61 each of which captures one microbead are formed, and a part other than the microwells 61 is shielded from light by the light shielding metal 62. Thus, when a microbead is captured by a part of the plurality of microwells 61 existing above the photodiode 12, the part of the microwells 61 is shielded from the excitation light by the microbead.

As a result, when the photon detection unit 13 detects the photon of the excitation light during irradiation of the excitation light, the number of microwells 61 each of which captures the microbead is increased, so that the number of photons incident on the photodiode 12 is reduced.

Here, in the present embodiment, since the part other than the part directly below the microwells 61 is shielded from light, all the light incident on the photodiode 12 enters the photodiode 12 by passing through the microwells 61. A proportion of the microwell 61 that captures the microbead in the plurality of microwells 61 is strongly correlated to the number of photons of the incident light. As a result, by measuring a quantity of the incident light of the excitation light, the proportion of the microwell 61 that captures the microbead in the microwells 61 above each of the photodiodes 12 is able to be estimated.

In a target molecule estimating method described in Embodiment 4 described above, a minimum concentration of a target that can be detected is decided by a total number of microbeads that are able to be tested in a molecular testing That is, in the target molecule estimating method described in Embodiment 4 described above, as illustrated in FIG. 6, a microbead that captures a target molecule and a microbead that does not capture a target molecule are captured in the microchamber of the microwell 31. Then, the number of target molecules is estimated from the quantity of the light in the photodiode from which the fluorescence is detected. Thus, as the number of microbeads captured in the microchamber is increased, the minimum concentration of the target that can be detected is reduced. That is, measurement of the target molecule with a low concentration is able to be performed.

For example, when the total number of beads that are able to be tested is ten thousand, a target molecule captured by one of the ten thousand microbeads can be detected. On the other hand, when the total number of beads is hundred thousand, a target molecule captured by one of the hundred thousand microbeads can be detected. Thus, measurement. of the target molecule with a low concentration is able to be performed.

Here, to quantify the concentration of the target molecule that is detected, it is necessary to calculate the total number of microbeads that are actually tested. For example, even when the total number of microbeads that are able to be tested is ten thousand, the number of microbeads that are actually captured may be 1000 and the fluorescence may be detected from the microchamber that captures one of the microbeads. In this case, the concentration indicating that one of the 1000 microbeads captures the target molecule is obtained. However, the concentration is different from a concentration indicating that one of the ten thousand microbeads captures the target molecule.

In the present embodiment, the size of the microwell 61 is optimized so that only one microbead is captured and the light quantity of the excitation sight incident on the photodiode 12 is measured. Such a configuration makes it possible to estimate the proportion of the microwell 61 that captures the microbead in the microwells 61 above the photodiode 12. Thereby, it is possible to estimate the number of microbeads captured above each of the photodiodes 12 and estimate a total number of microbeads that are tested. This makes it possible to enhance quantification of the test.

Moreover, in the present embodiment, the plurality of microwells 61 are formed above each of the photodiodes 12, so that the total number of microbeads that are able to be tested is able to be increased. This leads to reduction in the concentration of the target molecule that is able to be detected.

In this manner, in the fluorescent testing system 4 in the present embodiment, the plurality of microwells 61 as the through holes are provided above the photodiode 12. Note that, each of the microwells 61 preferably has a size by which one test object is held.

Thereby, it is possible to increase the number of test objects held in the microwells 61 and reduce the concentration of the target that is able to be detected. In particular, when each of the microwells 61 has a size by which one test object is held, an accurate concentration of the test object is able to be obtained.

Moreover, in the fluorescent testing system 4 in the present embodiment, the light shielding metal 62 as the metal layer for light shielding is formed above the photodiode 12 other than the part directly below the microwells 61.

Thereby, only the excitation light L1 passing through the microwells 61 serves as the light incident on the photodiode 12. As a result, it is possible to prevent stray light from outside from being incident on the photodiode 12.

Moreover, the fluorescent testing method in the present embodiment is a fluorescent testing method using the fluorescent testing system 4 of the present embodiment, and includes the photon detection step of detecting the photon of the excitation light L1 incident on the photodiode 12 during irradiation of the excitation light L1 and a fluorescence detection step of detecting, after extinguishment of the excitation light L1, fluorescence emitted from the test object after the excitation light L1 is radiated.

Thereby, only the fluorescence emitted from the test object is able to be measured by the fluorescence detection step without separating the excitation light L1 and the fluorescence by an optical filter.

Moreover, in the present embodiment, the plurality of microwells 61 are provided above the photodiode 12. Thus, in a case where a test object is held in a microwell 61, the photon of the excitation light L1 is blocked by the test object, and in a case where no test object is held in the microwell 61, the photon of the excitation light L1 is incident on the photodiode 12. As a result, by providing the photon detection step of detecting the photon of excitation light L1 incident on the photodiode 12 during irradiation of the excitation light L1, the number of test objects is able to be estimated.

Moreover, the fluorescent testing method in the present embodiment includes a liquid flowing step of causing liquid including a biological or nonbiological fine particle which is a test object to flow in the microfluidic channel 22 formed in the fluorescent testing system 4, and an estimation step of estimating, on the basis of information of the photon of the excitation light L1 detected at the photon detection step, the number of microwells 61 each of which captures the fine particle among the microwells 61 formed above the photodiode 12.

Thereby, by the estimation step, it is possible to estimate, on the basis of the information of the photon of the excitation light L1 detected at the photon detection step, the number of microwells 61 each of which captures the fine particle among the microwells 61 formed above the photodiode 12.

Accordingly, it is possible to obtain an accurate concentration of the test object.

Conclusion

A fluorescent testing system 1 to 4 in an aspect 1 of the invention includes: an excitation light source 23 that radiates excitation light L1 to a test object; a silicon integrated circuit 10 including a photon detection unit 13 that detects light by a photodiode 12; a holding layer 30, 40, 60 including at least one through hole (microwell 31, 41, 61) that is provided above the photodiode 12 and holds the test object; and a control unit 24 that causes the excitation light source 23 to radiate the excitation light L1 to the test object that is held and causes the photon detection unit 13, after extinguishment of the excitation light L1, to detect fluorescence emitted from the test object.

According to the aspect of the invention, the fluorescent testing system includes the excitation light source that radiates the excitation light to the test object, the silicon integrated circuit including the photon detection unit that detects light by the photodiode, and the holding layer including the through hole that is provided above the photodiode and holds the test object.

In such a kind of fluorescent testing system of the related art, by utilizing a difference of a wavelength of the excitation light and a wavelength of the fluorescence, the excitation light and the fluorescence are separated by an optical filter to detect only the fluorescence. Thus, only a fluorescent material suitable for an incorporated filter is able to be used for the test and there is a disadvantage that an application range of a type of the fluorescence is limited.

Here, a phenomenon of the fluorescence is such that a molecule and an ion that absorb ultraviolet light, visible light, or the like are excited, and then, the molecule and the ion are shifted to an intermediate excited state to emit light having a wavelength longer than that of the excitation light therefrom and are returned to a ground state, and an average time during which the excited state is returned to the ground state is called a fluorescent lifetime. Accordingly, by using the fluorescent lifetime, the fluorescence that is emitted is able to be observed after the extinguishment of the excitation light without using an optical filter that separates the excitation light and the fluorescence on the basis of the wavelengths.

Thus, in the invention, in a case where the test object that emits the fluorescence is detected, the excitation light source is caused to radiate the excitation light to the test object and the photon detection unit is caused, after the extinguishment of the excitation light, to detect the fluorescence emitted from the test object.

As a result, only the fluorescence is detected by the photon detection unit after the extinguishment of the excitation light. Thus, it is possible to measure only the fluorescence emitted from the test object without separating the excitation light and the fluorescence by an optical filter. Accordingly, it is not necessary to use an optical filter corresponding to a type of the fluorescence, thus making it possible to prevent complication of the fluorescent testing system.

Moreover, in the fluorescent testing system of the aspect of the invention, the photon detection unit by the photodiode is integrated in the silicon integrated circuit, and the chamber formed by the through hole that is small is formed on the photodiode, so that a fluorescent signal from the test object which is held in each chamber is able to be automatically detected.

As a result, neither a fluorescent microscope that causes enlargement and complication of the fluorescent testing system nor image processing for counting the number of times of detection from a fluorescent image that is observed is required, so that digital measurement such as counting of a desired test object is able to be easily performed.

Accordingly, it is possible to provide the fluorescent testing system that can avoid enlargement and complication.

In the fluorescent testing system 2 in an aspect 2 of the invention, at least a part of the holding layer 40 is formed by using silicon dioxide ($SiO_2$) in the fluorescent testing system in the aspect 1. Note that, the at least a part refers to a part of the holding layer, which is near the photodiode.

For example, in a case where the holding layer is formed by a material that emits fluorescence, both the fluorescence from the test object and the fluorescence from the holding layer are incident on the photodiode, so that the fluorescence from the test object is not able to be accurately detected.

On the other hand, since silicon dioxide ($SiO_2$) does not emit fluorescence, there is no possibility of confusion with the fluorescence from the fluorescence included in the test object and it is possible to achieve improvement of accuracy of detection of the fluorescence.

In the fluorescent testing system 2 in an aspect 3 of the invention, it is preferable that a lid (transparent plate 42) having a partition wall 42b is provided and is movable toward a direction of the holding layer 40, and when the lid (transparent plate 42) is moved to make the partition wall 42b contact with the holding layer 40, an isolation room (microchamber 43) that isolates the test object is formed by a recess (concavity 42c), formed by the lid (transparent plate 42) having the partition wall 42b, and the at least one through hole (microwell 41) of the holding layer 40, in the fluorescent testing system in the aspect 1 or 2.

Thereby, though it is difficult to form a deep through hole in the holding layer made from silicon dioxide ($SiO_2$), it is possible to increase the depth of the chamber that is the isolation room with the concavity formed by the lid that faces the holding layer and has the partition wall.

In the fluorescent testing system 3 in an aspect 4 of the invention, it is preferable that a heater 52 and a temperature sensor 53 are built in the silicon integrated circuit 10, in the fluorescent testing system in the aspect 1, 2, or 3.

Thereby, temperature control of a limited region including the test object included in the chamber is able to be performed. As a result, accurate temperature control is able to be performed at a higher speed in comparison with a case of the related art where temperature of an environment including a device is controlled.

A molecular testing method in an aspect 5 of the invention includes performing gene amplification reaction in a plurality of isolation rooms in parallel by using the fluorescent testing system described above.

According to the aspect of the invention described above, measurement values in many chambers are averaged, so that the initial number of DNA is able to be estimated with high accuracy, in comparison with gene amplification reaction that amplifies a specific gene by using normal gene amplification reaction.

Moreover, the initial number of DNA is able to be estimated even when there is no negative chamber, in comparison with a known digital PCR method. As a result, dynamic range of a concentration of DNA to which test is applicable is able to be enlarged.

Thus, it is possible to provide the molecular testing method using the fluorescent testing system that can avoid enlargement and complication.

A molecular testing method in an aspect 6 of the invention is a molecular testing method using the fluorescent testing system 1 in the aspect 1, and includes: a first step of mixing a microbead having a capture antibody with a detection antibody, further combining a captured target molecule with the detection antibody, and causing solution, which includes the microbead, to flow in a microfluidic channel 22 provided in the fluorescent testing system 1 in the aspect 1; a second step of causing a fluorescent substrate to flow in the microfluidic channel 22; a third step of causing oil to flow in the microfluidic channel 22; and a fourth step of detecting, by the fluorescent testing system 1, a fluorescent material generated when the fluorescent substrate reacts with an enzymatic label.

Thereby, it is possible to provide the molecular testing method in which detection and quantification of specific protein are performed with higher sensitivity and higher accuracy in comparison with a known ELISA method. It is also possible to provide the molecular testing method using the fluorescent testing system 1 that can avoid enlargement and complication.

In the fluorescent testing system 4 in an aspect 7 of the invention, the at least one through hole includes a plurality of through holes (microwells 61) provided above the photodiode 12. Note that, each of the through holes preferably has a size by which one test object is held.

Thereby, it is possible to increase the number of test objects held in the through holes and reduce the concentration of a target that is able to be detected. In particular, when each of the through holes has a size by which one test object is held, an accurate concentration of the test object is able to be obtained.

In the fluorescent testing system 4 in an aspect $ of the invention, a metal layer for light shielding (light shielding metal 62) is formed above the photodiode 12 other than a part directly below the at least one through hole (microwell 61).

Thereby, only the excitation light passing through the through holes serves as the incident light on the photodiode. As a result, it is possible to prevent stray light from outside from being incident on the photodiode.

A fluorescent testing method in an aspect 9 of the invention is a fluorescent testing method using the fluorescent testing system 4 described above, and includes: a photon detection step of detecting a photon of excitation light L1 incident on the photodiode 12 during irradiation of the excitation light L1; and a fluorescence detection step of detecting, after extinguishment of the excitation light L1, fluorescence emitted from the test object after the excitation light L1 is radiated.

Thereby, only the fluorescence emitted from the test object is able to be measured by the fluorescence detection step without separating the excitation light and the fluorescence by an optical filter.

In the aspect of the invention, the plurality of through holes are provided above the photodiode. Thus, in a case where the test object is held in a through hole, the photon of the excitation light is blocked by the test object, and in a case where no test object is held in the through hole, the photon of the excitation light is incident on the photodiode. As a result, by providing the photon detection step of detecting the photon of excitation light incident on the photodiode during irradiation of the excitation light, the number of test objects is able to be estimated.

The fluorescent testing method in an aspect 10 of the invention preferably includes: a liquid flowing step of causing liquid including a biological or nonbiological fine particle which is a test object to flow in the microfluidic channel 22 formed in the fluorescent testing system 4; and an estimation step of estimating, based on information of the photon of the excitation light L1 detected at the photon detection step, the number of through holes (microwells 61) in which the fine particle is captured among the plurality of through holes (microwells 61) formed above the photodiode 12, in the fluorescent testing method described above.

Thereby, by the estimation step, it is possible to estimate, on the basis of the information of the photon of the excitation light detected at the photon detection step, the number of through holes in which the fine particle is captured among the through holes formed above the photodiode.

Accordingly, it is possible to obtain an accurate concentration of the test object.

Note that, the invention is not limited to each of the embodiments described above, and may be modified in various manners within the scope indicated in the claims and an embodiment achieved by appropriately combining technical means disclosed in each of different embodiments is also encompassed in the technical scope of the invention. Further, by combining the technical means disclosed in each of the embodiments, a new technical feature may be formed.

REFERENCE SIGNS LIST 1 to 4 fluorescent testing system
10 silicon integrated circuit
11 silicon circuit board
12 photodiode
13 photon detection unit
13a first photon detection. unit
13h second photon detection unit
15 wire embedding layer
21 transparent plate (lid)
22 microfluidic channel
23 excitation light source
24 control unit
30 holding layer
31 microwell (through hole)
40 holding layer
41 microwell (through hole)
42 transparent plate (lid)
42a lid
42b partition wall
42c concavity (recess)
43 microchamber (isolation. room)
51 microchamber (isolation room)
52 heater
53 temperature sensor
60 holding layer
61 microwell (through hole)
62 light shielding metal (metal layer for light shielding)
L1 excitation light The inventioon claimed is:

1. A fluorescent testing system comprising:
an excitation light source that radiates excitation light to a test object;
a silicon integrated circuit including a photon detection unit that detects light by a photodiode;
a holding layer including at least one through hole that is provided above the photodiode and holds the test object;
a control unit that causes the excitation light source to radiate the excitation light to the test object that is held and causes the photon detection unit, after extinguishment of the excitation light, to detect fluorescence emitted from the test object; and
a lid having a partition wall is provided at a position facing the holding layer and is movable toward a direction of the holding layer, and when the lid is moved to make the partition wall contact with the holding layer, an isolation room that isolates the test object is formed by a recess, formed by the lid having the partition wall, and the at least one through hole of the holding layer.

2. A fluorescent testing system comprising:
   an excitation light source that radiates excitation light to a test object;
   a silicon integrated circuit including a photon detection unit that detects light by a photodiode;
   a holding layer including at least one through hole that is provided above the photodiode and holds the test object;
   a control unit that causes the excitation light source to radiate the excitation light to the test object that is held and causes the photon detection unit, after extinguishment of the excitation light, to detect fluorescence emitted from the test object; and
   a heater and a temperature sensor are built in the silicon integrated circuit.

3. A molecular testing method comprising a step of performing gene amplification reaction in a plurality of isolation rooms each of which isolates a test object in parallel by using the fluorescent testing system according to claim 2.

4. A fluorescent testing system comprising:
   an excitation light source that radiates excitation light to a test object;
   a silicon integrated circuit including a photon detection unit that detects light by a photodiode;
   a holding layer including at least one through hole that is provided above the photodiode and holds the test object;
   a control unit that causes the excitation light source to radiate the excitation light to the test object that is held and causes the photon detection unit, after extinguishment of the excitation light, to detect fluorescence emitted from the test object; and
   the at least one through hole includes a plurality of through holes provided above the photodiode.

5. A fluorescent testing method using the fluorescent testing system according to claim 4, the fluorescent testing method comprising:
   a photon detection step of detecting a photon of excitation light incident on the photodiode during irradiation of the excitation light;
   a fluorescence detection step of detecting, after extinguishment of the excitation light, fluorescence emitted from the test object after the excitation light is radiated;
   a liquid flowing step of causing liquid including a biological or nonbiological fine particle which is a test object to flow in a microfluidic channel formed in the fluorescent testing system; and
   an estimation step of estimating, based on information of the photon of the excitation light detected at the photon detection step, the number of through holes in which the fine particle is captured among the plurality of through holes formed above the photodiode.

* * * * *